US010435269B2

(12) United States Patent
Pasteels

(10) Patent No.: US 10,435,269 B2
(45) Date of Patent: Oct. 8, 2019

(54) APPARATUS FOR KNOTTING DRAWSTRINGS OF MEDICAL DEVICES OR MEDICAL DEVICES CONTAINING DRUGS

(75) Inventor: Pierre Pasteels, B-Soumagne (BE)

(73) Assignee: Odyssea Pharma S.P.R.L., Grace-Hollogne (BE)

(*) Notice: Subject to any disclaimer, the term of this patent is extended or adjusted under 35 U.S.C. 154(b) by 371 days.

(21) Appl. No.: 13/980,107

(22) PCT Filed: Feb. 8, 2012

(86) PCT No.: PCT/EP2012/052087
§ 371 (c)(1),
(2), (4) Date: Jul. 17, 2013

(87) PCT Pub. No.: WO2016/107464
PCT Pub. Date: Aug. 16, 2012

(65) Prior Publication Data
US 2013/0298361 A1 Nov. 14, 2013

Related U.S. Application Data

(60) Provisional application No. 61/484,910, filed on May 11, 2011.

(30) Foreign Application Priority Data

Feb. 8, 2011 (EP) .................................. 11153641

(51) Int. Cl.
B65H 69/04 (2006.01)
A61F 13/20 (2006.01)

(52) U.S. Cl.
CPC .......... B65H 69/04 (2013.01); A61F 13/2082 (2013.01)

(58) Field of Classification Search
CPC .. D04G 3/02; D04G 5/00; A01F 15/12; A61B 17/0469; B65H 69/04; A61M 25/0147; A61F 13/2082
USPC ........... 289/2, 17, 3, 1.2; 128/830, 833, 839; 28/149
See application file for complete search history.

(56) References Cited

U.S. PATENT DOCUMENTS 1,815,546 A * 7/1931 Brownlee ................ D04G 1/00
289/3
2,000,504 A * 5/1935 Emile .................... B65H 69/04
289/3

(Continued)

FOREIGN PATENT DOCUMENTS

| EP | 2383377 | * | 4/2010 |
| GB | 2250032 | * | 5/1992 |
| GB | 2250032 A | | 5/1992 |
| NL | 1020221 | | 9/2003 |

OTHER PUBLICATIONS

Machine translation of EP2383377 (Kuhl et al.) Nov. 2, 2011, provided by espacenet and google, retrieved Oct. 5, 2015.*

(Continued)

Primary Examiner — Sally Haden
Assistant Examiner — Jillian K Pierorazio
(74) Attorney, Agent, or Firm — Amster, Rothstein & Ebenstein LLP

(57) ABSTRACT

The present invention provides an apparatus for making knots in flexible element attached to a medical device and methods using said apparatus.

22 Claims, 2 Drawing Sheets

(56) References Cited

U.S. PATENT DOCUMENTS

| | | | | |
|---|---|---|---|---|
| 2,072,668 A * | 3/1937 | Eltgroth | | D04B 17/00 66/4 |
| 2,150,023 A * | 3/1939 | Clack | | D04G 3/02 112/410 |
| 2,245,903 A * | 6/1941 | Cone | | D04D 7/06 223/46 |
| 2,270,619 A * | 1/1942 | Bowyer | | D04B 39/00 66/4 |
| 2,462,957 A * | 3/1949 | Gunn | | A22C 11/122 289/2 |
| 2,487,200 A * | 11/1949 | Trager | | A61F 13/2065 604/385.18 |
| 2,624,957 A * | 1/1953 | Collins | | G09B 25/00 289/17 |
| 2,773,713 A * | 12/1956 | Smalley | | A01K 91/04 289/17 |
| 2,821,421 A * | 1/1958 | Smith | | B65H 69/04 289/17 |
| 2,865,665 A * | 12/1958 | Messa | | B65H 69/04 289/17 |
| 2,873,133 A * | 2/1959 | Wieser | | A61F 13/2085 289/3 |
| 3,006,232 A * | 10/1961 | Lindholm | | D04G 5/00 87/53 |
| 3,223,440 A * | 12/1965 | Rosenzweig | | D04D 7/10 223/46 |
| 3,239,258 A * | 3/1966 | Banks | | A61F 13/2085 112/470.22 |
| 3,307,864 A * | 3/1967 | Rosenzweig | | D04B 7/06 289/1.2 |
| 3,333,877 A * | 8/1967 | Born | | B65B 13/26 289/1.5 |
| 3,377,674 A * | 4/1968 | Brassaw | | D04D 5/00 28/147 |
| 3,406,994 A * | 10/1968 | Duncker | | B65H 69/04 289/2 |
| 3,678,709 A * | 7/1972 | Nowicki | | D04B 39/00 66/4 |
| 3,695,271 A * | 10/1972 | Chodorow | | A61B 17/0466 606/233 |
| 3,712,651 A * | 1/1973 | Shockley | | A01K 91/04 289/17 |
| 3,713,680 A * | 1/1973 | Pagano | | A01K 91/04 289/17 |
| 3,794,025 A * | 2/1974 | Lerner | | A61F 6/148 128/840 |
| 3,814,469 A * | 6/1974 | Simon | | A61F 13/2085 28/120 |
| 3,845,761 A * | 11/1974 | Zaffaroni | | A61F 6/144 128/833 |
| 3,913,573 A * | 10/1975 | Gutnick | | A61F 6/144 128/833 |
| 3,973,560 A * | 8/1976 | Emmett | | A61F 6/142 128/833 |
| 4,233,968 A * | 11/1980 | Shaw, Jr. | | A61F 6/16 128/833 |
| 4,248,063 A * | 2/1981 | Wang | | D04B 3/00 66/4 |
| 4,284,074 A * | 8/1981 | Shaw, Jr. | | A61K 9/0039 128/833 |
| 4,403,797 A * | 9/1983 | Ragland, Jr. | | A01K 91/04 289/17 |
| 4,454,968 A * | 6/1984 | StLawrence | | D04D 11/00 223/46 |
| 4,528,217 A * | 7/1985 | Spathis | | D04D 7/10 223/46 |
| 4,578,076 A * | 3/1986 | Luukkainen | | A61D 1/06 128/833 |
| 4,708,134 A * | 11/1987 | Wildemeersch | | A61F 6/142 128/840 |
| 4,774,108 A * | 9/1988 | Cano | | B44C 1/04 140/107 |
| 4,836,587 A | 6/1989 | Hinzmann | | |
| 4,871,200 A * | 10/1989 | Ryder | | A01K 91/04 289/17 |
| 4,949,732 A * | 8/1990 | Spoon | | A61F 6/18 128/839 |
| 5,098,137 A * | 3/1992 | Wardall | | A01K 91/04 289/17 |
| 5,104,160 A * | 4/1992 | Cheng | | A63H 27/10 289/1.5 |
| 5,143,125 A * | 9/1992 | Tamatani | | B65H 49/12 139/450 |
| 5,217,470 A * | 6/1993 | Weston | | A61B 17/0469 289/1.2 |
| 5,240,295 A * | 8/1993 | Spencer | | B65H 69/04 289/1.5 |
| 5,411,188 A * | 5/1995 | Teuten | | D04D 7/10 223/44 |
| 5,562,456 A * | 10/1996 | Cianciotto | | A41D 25/08 289/17 |
| 5,566,435 A | 10/1996 | Brown, Jr. | | |
| 5,626,148 A * | 5/1997 | Lehtinen | | A61F 6/14 128/830 |
| 5,882,051 A * | 3/1999 | Dreger | | A63H 27/10 289/17 |
| 6,015,172 A * | 1/2000 | Williams | | A41D 25/08 223/DIG. 1 |
| 6,131,778 A * | 10/2000 | Etzion | | D04D 7/10 223/46 |
| 6,171,317 B1 * | 1/2001 | Jackson | | A61B 17/0469 289/17 |
| 6,213,040 B1 * | 4/2001 | Shepard | | A61F 13/2085 112/470.21 |
| 6,648,378 B1 * | 11/2003 | Torres | | B65B 13/025 289/1.2 |
| 6,779,817 B2 * | 8/2004 | Ota | | B44C 5/00 289/17 |
| 7,048,748 B1 * | 5/2006 | Ustuner | | A61B 17/0482 606/139 |
| 8,157,297 B2 * | 4/2012 | Spilbor | | G09B 19/0076 289/17 |
| 8,573,656 B1 * | 11/2013 | Zhang | | A01G 17/08 289/2 |
| 9,635,847 B1 * | 5/2017 | Chaney | | A01K 97/26 |
| 2003/0020280 A1 * | 1/2003 | Hakimain | | A41D 25/025 289/2 |
| 2003/0197040 A1 * | 10/2003 | West, Sr. | | A41G 1/02 223/46 |
| 2003/0197041 A1 * | 10/2003 | West, Sr. | | A41G 1/02 223/46 |
| 2007/0203508 A1 * | 8/2007 | White | | A61B 17/0401 606/148 |
| 2007/0239275 A1 * | 10/2007 | Willobee | | A61F 2/08 623/13.17 |
| 2008/0265576 A1 * | 10/2008 | May-Newman | | G09B 19/003 289/1.5 |
| 2010/0318105 A1 * | 12/2010 | Jayant | | A61B 17/12013 606/148 |
| 2011/0017219 A1 * | 1/2011 | de Graaff | | A61F 6/14 128/833 |
| 2011/0033519 A1 * | 2/2011 | Leong | | A61F 6/144 424/432 |
| 2012/0326441 A1 * | 12/2012 | Frew | | A01K 91/04 289/1.5 |
| 2013/0181447 A1 * | 7/2013 | Romagnoli | | B65B 29/04 289/1.5 |

OTHER PUBLICATIONS

The International Search Report dated Oct. 4, 2012 for PCT Application No. PCT/EP2012/052087.

* cited by examiner

US 10,435,269 B2

APPARATUS FOR KNOTTING DRAWSTRINGS OF MEDICAL DEVICES OR MEDICAL DEVICES CONTAINING DRUGS

CROSS-REFERENCE TO RELATED APPLICATIONS

This application is a U.S. national phase of PCT Application No. PCT/EP2012/052087, filed Feb. 8, 2012, which claims priority to European Application No. EP 11153641.3, filed Feb. 8, 2011 and U.S. Provisional Application No. 61/484,910, filed May 11, 2011.

FIELD OF THE INVENTION

The invention relates to methods and apparatuses for making knots in flexible elements, particularly in withdrawal cords or strings, pull strings, drawstrings or positioning strings of medical devices.

BACKGROUND OF THE INVENTION

It is well-known that devices such as hormonal or copper intra-uterine devices (IUD), which are used as a common method of anti-conception and/or for treatment of menorrhagia, have a string attached to the device. Similarly, tampons also have a withdrawal cord, which is affixed to the tampon by making a knot in said cord. After insertion of a T-shaped IUD, the string remains positioned within the cervix for a period of 5 to 10 years to facilitate extraction of the IUD by the health care provider. It is customary to provide the string of an IUD with a knot to securely fasten the string.

During the history of development of Cu-IUD, specific attention has been brought on the thread and on the knot. The Dalkon Shield tails experience in US in the 1970s established that pelvic infection (which could ultimately lead to death of the woman) may be attributed to the multifilament thread connected to the device. Ever since, the field has been more cautious about the details of the string and knot connected to medical devices. More specifically, the knot should not hamper the correct insertion of the device, it should not hamper the efficacy of the device nor should it have a negative impact on the safety of the device. In addition, it should be durable enough to allow for a correct removal of the device after several years.

The type, the positioning, the resistance, the strength of attachment and the stability all over the duration of use of the device may have great impact on the global quality of the device. The manufacturing of a device of adequate quality imposes a close control of all these parameters and a high reproducibility in the process of making the knot. Typical examples are the copper- or hormone (e.g. levonorgestrel) based IUDs. In this case, the length of string between knot and IUD is crucial as well as the type and thickness of the knot, because the knot can block the delivery of the IUD when e.g. applied through an applicator tube or device.

Furthermore, the type, the positioning, the resistance and the thickness of the knot are of crucial importance for the correct use of the device at the insertion step or at the removal steps. In addition, the strength of the attachment of the flexible element to the IUD is influenced by the form of the knot.

Finally, the position of the knot with respect to the IUD and its form and thickness will also be important to avoid spreading of possible infectious agents such as viruses, bacteria and fungi from the vaginal region into the uterus, since it has been observed that said knot can be the thriving place of infectious agents (cf. e.g. Roberts at al., 1984, Contraception 29(3):215-28; Rivera at al., 1993, Curr Opin Obstet Gynecol 5(6):829-32).

Currently, the flexible elements or wires are mostly tied manually to the IUDs, because of the importance to have a reproducible knot at the correct position. A drawback of presently known methods for making such knots is that they are too slow and labor-intensive. Furthermore, they are prone to human error and batch to batch differences.

Some methods of automating the knot-forming process are known for e.g. tampons. However, they are all quite complex. We refer for example to U.S. Pat. Nos. 4,836,587 and 5,566,435, describing an apparatus to knot tampon strings using rather complex devices. The present invention provides an alternative device and method to make knots in flexible elements of medical devices or medical devices containing drugs, which is easy to handle, cheap and very effective in positioning and shaping of the knot vis-à-vis the device.

SUMMARY OF THE INVENTION

An object of the invention is to provide a simple and inexpensive apparatus for making knots in flexible elements at a high frequency and with a high degree of predictability.

Another object of the invention is to allow the apparatus to make knots at different positions of the flexible element by simple adjustment of only one parameter of the apparatus.

Another object of the invention is to allow the apparatus to make knots varying in type and thickness by simple adjustment of the procedure performed by the apparatus.

Another object of the invention is to construct and assemble the apparatus in such a way that it can be readily automated and integrated into existing production lines for devices.

The inventors have surprisingly found that these objects can be met either individually or in any combination by the apparatus and method according to the invention. The inventors have also found that these objects can be met either individually or in any combination by preferred embodiments of the apparatus and method according to the invention.

In a preferred embodiment, the invention provides an apparatus (20) for making a knot in a flexible element attached to a device, comprising: (i) a guiding means (ABC) for guiding the element (2) fixed to the device (1), wherein guiding means (ABC) forms a geometrical figure which is large enough to contain the device (1); (ii) a first position (10) outside the geometrical figure formed by guiding means (ABC), to which the device (1) can be affixed; (iii) a second position (10') to which the device (1) can be affixed, for example after being lifted over or under the closed loop(s) to form a relatively loose knot in the element, wherein said second position (10') is inside the geometrical figure formed by guiding means (ABC); (iv) means for tightening the knot through a tensioning means (40); wherein the guiding means (i), the first position (ii) and the second position (iii) can be rotated with respect to the means for tightening (iv).

In a preferred embodiment, guiding means (ABC) is a single continuous guiding means, or is constituted out of several individual guiding means, which can form any geometrical shape allowing for the making of a loose loop around the device (1).

In a preferred embodiment of the invention, guiding means (ABC) comprises at least 3 individual guiding means parts A, B and C, preferably forming a triangle.

In an alternative embodiment, guiding means (ABC) comprises 2 individual guiding means parts A and BC, which together can form any geometrical shape allowing for the making of a loose loop.

In a more specific embodiment of the apparatus (20) according to the invention, the guiding means (ABC) can be retracted into or lifted away partially or fully from the apparatus (20) in order to release element (2). This can be done in either a single step, in which all parts of the guiding means are retracted or lifted at the same time, or in several steps, wherein each component of the guiding means is retracted or lifted individually.

In a more specific embodiment, the apparatus (20) according to the invention additionally comprises a translating means, capable of translating the device from the first position (10) to the second position (10'), by lifting the device over (or under) and inside the one or more closed loops formed in the element (2) by the apparatus (20).

In a more specific embodiment of the apparatus (20) according to the invention, the diameter and/or the location of part A of the guiding means (ABC), preferably located closest to the device (1), with respect to the second position (10') defines the length of the element between knot and device.

Alternatively or in combination herewith, the diameter and/or location of the second position (10') of the device with respect to the guiding means (ABC), defines the length of the element between the knot and the device.

In a more specific embodiment of the apparatus (20) according to the invention, the one or more strands of the element (2) are under constant tension, e.g. by means of a tensioning means (40).

In a more specific embodiment of the apparatus (20) according to the invention, one or more strands of the element are directed towards or away from the guiding means (ABC) by tensioning means (40).

In a more specific embodiment of the apparatus (20) according to the invention, part A of the guiding means (ABC) is located closest to the end of the device (1) whereon the element (2) is fixed.

In a more specific embodiment of the apparatus (20) according to the invention, the element (2) is provided to the apparatus (20) in the form of a spindle or bobbin, preferably capable of maintaining a certain tension on the element.

In another embodiment of the apparatus (20) according to the invention, the element (2) is provided to the apparatus (20) already cut beforehand.

In a more specific embodiment of the apparatus (20) according to the invention, the and of element (2) is held under constant tension by a tensioning means (40).

In a more specific embodiment of the apparatus (20) according to the invention, all movements or rotations of the apparatus (20) are automated.

In a more specific embodiment of the apparatus (20) according to the invention, said translating means is a robotic arm.

The invention further provides for a method for making a knot in a flexible element connected to a device using the apparatus (20) according to the present invention, comprising the steps of:

a) placing the device (1), to which the element (2) is attached, in the first position (10) on the apparatus (20), outside the area defined by guiding means (ABC);

b) the guiding means (ABC) effectuates one or more rotations with respect to the tensioning means (40), thereby forming one or more closed loops in element (2);

c) the device (1) is translated from its first position (10) to its second position (10') inside the area defined by guiding means (ABC), by lifting it over or under and into the closed loop(s) formed in step b);

d) guiding means (ABC) releases the element (2), which is pulled away by tensioning means (40), thereby forming the final knot (3).

Preferably, said flexible element is the drawstring of a medical device or a medical device containing drugs.

Preferably, the element (2) is cut to a desired length.

In a preferred embodiment of the method according to the invention, the number of rotations, translations and threading actions can be adjusted to tailor the thickness of the knot.

In a preferred embodiment of the method according to the invention, said method is automated. Preferably, the translation movement of device (1) is performed by a robotic arm.

In a preferred embodiment of the method according to the invention, guiding means (ABC) releases the element in two steps: firstly guiding means BC releases the element, after which guiding means A releases the element.

In a preferred embodiment of the method according to the invention, guiding means (ABC) releases the element in two or three steps: firstly guiding means B and C release the element (either simultaneously or consecutively), after which guiding means A releases the element.

In a particularly preferred embodiment of the apparatus (20) or method according to the invention, the device is an intra uterine device (IUD), for contraceptive or other intra-uterine treatment, tampons, hearing aids, and the like. In a particularly preferred embodiment, the apparatus (20) and methods according to the invention can be used to make a knot in the withdrawal cord of a Levonorgestrel secreting contraceptive IUD (cf. FIG. 2).

Although the invention will be described primarily with reference to the making and manipulation of strings of intra-uterine devices (IUD) and tampons, the apparatus (20) and method according to the present invention can of course be used with equal or similar advantage for the making of knots in flexible elements which can be secured to a wide variety of devices.

DETAILED DESCRIPTION OF THE INVENTION

Figure 1:
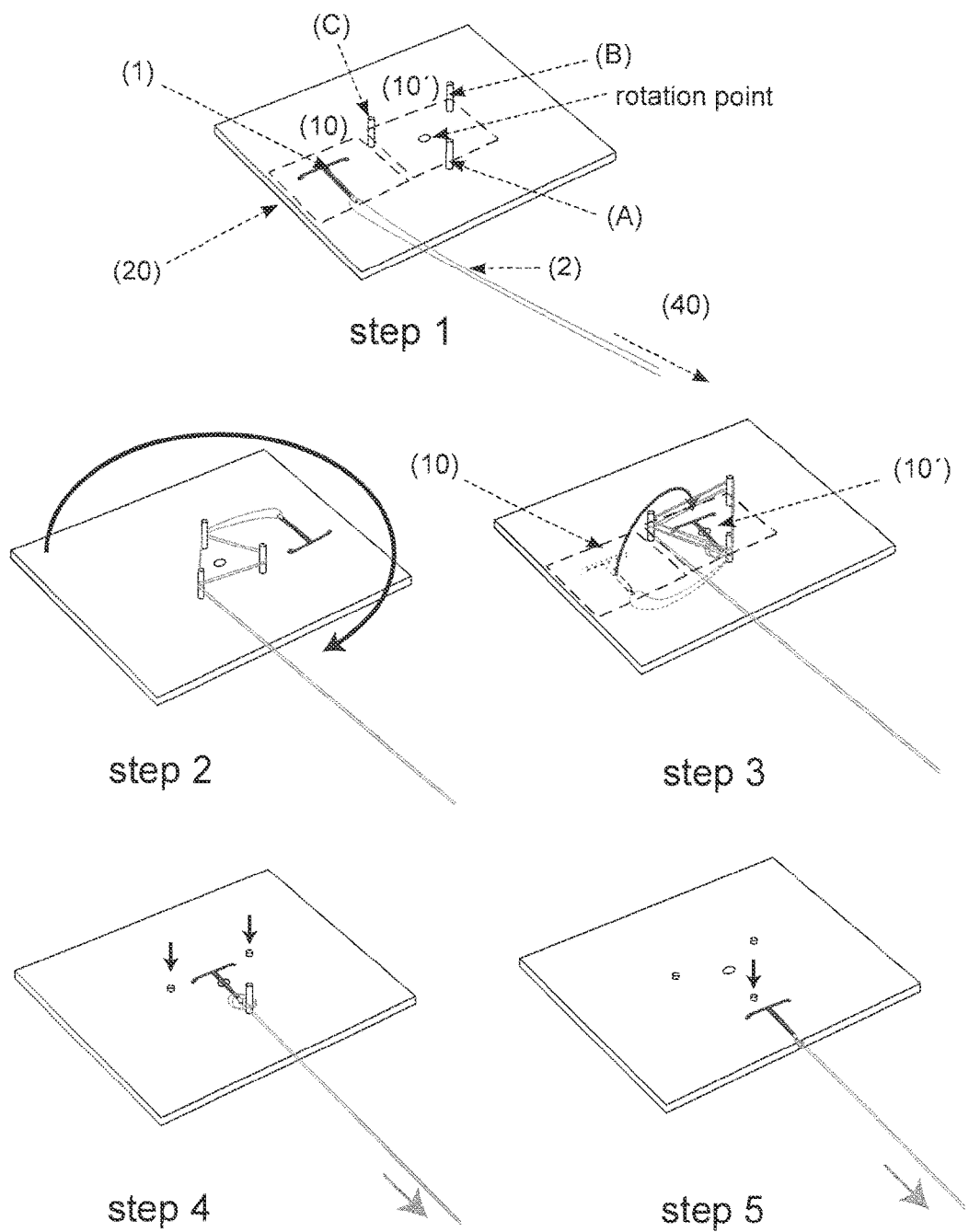
FIG. 1: Schematic representation of the knot making apparatus and the method performed thereby.
Figure 2:
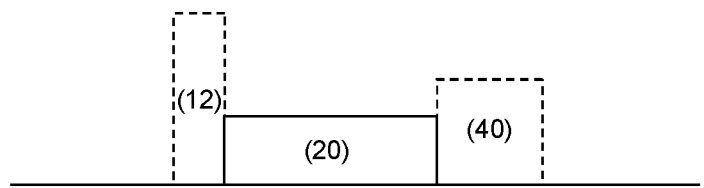
FIG. 2. Block diagram representation of the knot making apparatus (20), an optional robotic arm (12) for automation and for translation of the device (1), and an optional tensioning means (40).

Unless defined otherwise, all technical and scientific terms used herein have the same meaning as is commonly understood by one of skill in the art. All publications referenced herein are incorporated by reference thereto.

The articles 'a' and 'an' are used herein to refer to one or to more than one, i.e. to at least one of the grammatical object of the article.

Throughout this application, the term 'about' is used to indicate that a value includes the standard deviation of error for the device or method being employed to determine the value.

The recitation of numerical ranges by endpoints includes all integer numbers and, where appropriate, fractions subsumed within that range (e.g. 1 to 5 can include 1, 2, 3, 4 when referring to, for example, a number of elements). The recitation of end points also includes the end point values themselves (e.g. from 1.0 to 5.0 includes both 1.0 and 5.0)

Throughout this application, the terms 'device' or 'devices' are used to denote any object that is inserted into an external body orifice. Among these devices we consider, but do not limit ourselves to: intra-uterine devices (IUD) or intra-uterine systems (IUS), tampons, hearing aids. As far as IUD and IUS are concerned, the practical use (e.g. contraceptive, medicinal), optional additional components (e.g. antibiotics, antiseptics, hormones) and material (e.g. copper, silver, polyethylene) are not deemed critical for this invention.

Throughout this application, the terms 'element' or 'elements' are used to denote any flexible object that can be knotted. Among these elements we consider, but do not limit ourselves to: wires, cables, strings, ribbons, hairs, cords, chains, bands. Furthermore, the type of material in which these elements are fabricated is not deemed critical for this invention. This element can consist of one or multiple strands. The element may be present on e.g. a spindle or bobbin or be already cut beforehand. Said spindle or bobbin should be capable of retaining a certain amount of tension on the element.

Throughout this application, the term 'translating means' is used to denote any part of the apparatus that can be displaced in a translational fashion. Among these types of movement we consider, but do not limit ourselves to: sliding, rolling, dropping. Furthermore, the type of material in which these translating means are fabricated is not deemed critical for this invention. The translational movement is considered a relative movement between different parts of the apparatus, and not referred to a fixed point of reference.

Throughout this application, the term 'rotation' is used to denote any relative rotational movement between different parts of the apparatus, and not referred to a fixed point of reference. Among these types of movement we consider, but do not limit ourselves to: turning, twisting, spinning.

Throughout this application, the term 'guiding means' is used to denote any part of the apparatus that guides the flexible element along a certain element. The guiding means can form one geometric shape allowing the making of a loop, or can comprise several individual guiding means that together form a geometric shape allowing the making of a loop. Among these types of guiding means we consider, but do not limit ourselves to: bolts, hooks, clamps, arches, staples, holes, trenches, clasps and elements built therefrom. Furthermore, the type of material in which these guiding means are fabricated is not deemed critical for this invention.

Throughout this application, the term 'tensioning means' is used to denote any part of the apparatus that keeps the flexible element under constant tension. Among these types of tensioning means we consider, but do not limit ourselves to: coils, springs, weights, suction devices. Furthermore, the type of material in which these tensioning means are fabricated is not deemed critical for this invention.

Throughout this application, the term 'restraining means' is used to denote any part of the apparatus that keeps the translating means restrained to a certain position on the apparatus. Among these types of restraining means we consider, but do not limit ourselves to: studs, pins, hooks, bolts, clamps, clasps. Furthermore, the type of material in which these restraining means are fabricated is not deemed critical for this invention.

Throughout this application, the term 'releasing action' is used to denote any action that releases the flexible element from the guiding means. Among these types of releasing steps we consider, but do not limit ourselves to: lifting, retracting, sliding off.

Throughout this application, the term 'fixating means' is used to denote any part of the apparatus that keeps the device fixed to a certain position. Among these types of fixating means we consider, but do not limit ourselves to: studs, pins, hooks, bolts, clamps, clasps, adhesive tape, magnets. Furthermore, the type of material in which these fixating means are fabricated is not deemed critical for this invention.

In the following detailed description of the invention, reference is made to the accompanying drawings that form a part hereof, and in which are shown by way of illustration only of specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

In one embodiment, the apparatus (20) consists of two settings defined by a fixating means (10 and 10'), to which a device (1) is secured, while part of the apparatus (20) provides a rotational movement. The device is connected to an element (2), which is to be knotted. The end of the element (2) (all ends in case of multiple strands) is attached to a tensioning means (40), which maintains tension on the string. The apparatus (20) contains a guiding means (ABC) surrounding the fixating means (10'). Said guiding means (ABC) is placed in such a way that the surface area defined by the guiding means (ABC) is large enough to allow mechanical threading of the device (1) through said guiding means (ABC).

In a preferred embodiment of the invention, guiding means (ABC) comprises 3 individual guiding means A, B and C.

In an alternative embodiment, guiding means (ABC) forms one continuous guiding means, which can be any geometrical shape allowing for the making of a loose loop around device (1).

In an alternative embodiment, guiding means (ABC) comprises 2 individual guiding means A and BC, which together can form any geometrical shape allowing for the making of a loose loop around device (1).

If applicable, the diameter of part A of the guiding means and its position with respect to device (1) can define the position of the knot vis à vis the device (1) and can hence be optimized according to the preferred position of said knot for a certain application (i.e. will be dependent on the type of device).

The fixating means (10') ensure optimal placement of the device (1) and can serve to fine-tune the position of the knot vis à vis the device. Again, said position can help in optimizing said position of the knot for a certain application (i.e. will be dependent on the type of device).

During the first step (labeled as step 1 in FIG. 1), the device (1), to which the element is attached (2), is mounted on the fixating means (10). The starting position of the device (1) is outside the area defined by the guiding means (ABC), and restrained as such by the fixating means (10).

In a second step (labeled as step 2 in FIG. 1), the apparatus (20) effectuates one or more rotations, creating one or more loops of the element (2). The constant tension of the element (2) provided by the tensioning means (40) ensures that the loops remain tightened around the guiding means (ABC).

In a third step (labeled as step 3 in FIG. 1), the device (1) is released from the fixating means (10). The device (1) is subsequently re-attached to the second fixating means (10') from above the loops. This threading action effectively creates the knot (3).

In a fourth step (labeled as step 4 in FIG. 1), the element (2) is released from the guiding means B and C (or BC when combined in one means) by a releasing action. This action effectively tightens the knot (3) around guiding means A by the tension provided by the tensioning means (40). The position of the device (1) vis-à-vis the guiding means A will define the length of string between the device and the knot.

In a fifth step (labeled as step 5 in FIG. 1), the element (2) is released from guiding means A by a releasing action, tightening the final knot (3). The device is subsequently released from fixating means (10'). After these steps, the element (2) may be cut to desired length.

In an alternative embodiment of the invention, the guiding means B and C form one guiding means (BC) which undergoes a releasing action in the fourth step.

In an alternative embodiment of the invention, the guiding means A, B and C form one guiding means (ABC), which undergoes a releasing action in the fourth step and does not require the fifth step.

The type and thickness of the knot (3) can be varied by the number of rotations effectuated by the apparatus (20).

The length of the string between the device and the knot can be accurately defined by the final position of the fixating means (10') with respect to guiding means A. This can be achieved by either modifying the position of the fixating means (10'), or by modifying the position of guiding means A.

The number and positioning of the guiding means can be varied to better emulate the shape of the device (1) and ease the threading action. The order during which the guiding means undergo a releasing action with respect to the element (2) is not deemed critical for the invention. Nevertheless, a final releasing step from guiding means A is the preferred embodiment of the invention.

In one embodiment, the apparatus (20) consists of a translating means (10), which can provide a translational movement. This translating means (10) contains a setting (11) to which the device (1) can be secured. The device is connected to an element (2), which is to be knotted. The end of the element (2) (all ends in case of multiple strands) is attached to a tensioning means (40), which maintains tension on the string. The apparatus (20) contains a guiding means (ABC) adjacent to the translating means (10). Said guiding means (ABC) is placed in such a way that the surface area defined by the guiding means is large enough to allow mechanical threading of the device (1) through said guiding means (ABC).

The diameter and position of guiding means A will define the position of the knot vis à vis the device and can hence be optimized according to the preferred position of said knot for a certain application (i.e. will be dependent on the type of device).

Additional restraining means (50) ensure optimal placement of the translating means (10) on the apparatus (20) and can help in fine-tuning the position of the knot vis à vis the device. Again, said position can help in optimizing said position of the knot for a certain application (i.e. will be dependent on the type of device).

Below, a preferred embodiment of the method according to the invention is described:

During the first step, the device (1), to which the element is attached (2), is mounted on the setting (11) in the translating means (10). The starting position of the translating means (10) holding the device (1) is outside the area defined by the guiding means (ABC), labeled as position 1 in FIG. 1, and restrained as such by the restraining means (50).

In a second step, the apparatus (20) effectuates one or more rotations, creating one or more loops of the element (2). The constant tension of the element (2) provided by the tensioning means (40) ensures that the loops remain tightened around the guiding means (ABC).

In a third step, the device (1) is released from the translating means (10).

In a fourth step, the translating means (10), without the device, is moved under the loops, so that it is located in the area defined by the guiding means (ABC), and restrained as such by the restraining means (50).

In a fifth step, the device (1) is re-attached to the translating means (10) from above the loops. This threading action effectively creates the knot (3).

In an optional sixth step, the translating means (10), holding the device (1), is moved with respect to guiding means A to define the final length of the element between the knot (3) and the device (1), and restrained as such by the restraining means.

In a seventh step, the element (2) is released from the guiding means B and C by a releasing action. This action effectively tightens the knot (3) around guiding means A by the tension provided by the tensioning means (40).

In an eighth step, the element (2) is released from guiding means A by a releasing action, tightening the final knot (3).

In a final step, the element (2) is out to desired length and the device (1) is released from the translating means (10).

In an alternative embodiment of the invention, the guiding means B and C form one guiding means (BC).

In an alternative embodiment of the invention, the guiding means A, B and C form one guiding means (ABC), which undergoes a single releasing action in the seventh step and does not require the eighth step.

In essence, the invention provides a method for making a knot in a flexible element connected to a device using the apparatus (20) according to the invention comprising the steps of:

a) placing the device (1), to which the element (2) is attached, in the first position (10) on the apparatus (20), outside the area defined by guiding means (ABC);

b) rotating the guiding means (ABC) one or more times with respect to the tensioning means (40), thereby forming one or more closed loops in element (2);

c) translating the device (1) from its first position (10) to its second position (10') inside the area defined by guiding means (ABC), by lifting it over or under the closed loop(s) formed in step b);

d) releasing element (2) from guiding means (ABC), under constant tension by the tensioning means (40), thereby forming the final knot (3).

The type and thickness of the knot (3) can be varied by the number of rotations effectuated by the apparatus (20).

The type and thickness of the knot (3) can also be varied by the number of translations effectuated by the translating means (10).

The type and thickness of the knot (3) can furthermore be varied by the number of threading actions effectuated by release and re-attachment of the device (1) to the translating means (10).

The type and thickness of the knot (3) can be varied by any combination of rotations, translations and/or threading actions mentioned above in any order and/or repetition.

The length of the string can be accurately defined by the final position of the setting (11) on the translating means (10) with respect to guiding means A. This can be achieved by either optional step six, or by modifying the position of guiding means A.

The number and positioning of the guiding means can be varied to better emulate the shape of the device (1) and ease the threading action. The order during which the guiding means undergo a releasing action with respect to the element (2) is not deemed critical for the invention. Nevertheless, a final releasing step from guiding means A is the preferred embodiment of the invention.

The apparatus (20) of the invention can make knots while one or more ends of the flexible elements are already attached to the device. The apparatus (20) of the invention renders it possible to make knots in flexible elements each of which consists of two or more strands.

Examples of certain alternative embodiments according to the invention are given below.

In an embodiment, the invention relates to an apparatus (20) for making a knot in a flexible element (2) attached to a medical device (1), which optionally contains a drug, comprising:

(i) a guiding means (ABC) for guiding the element (2) fixed to the device (1), wherein guiding means (ABC) forms a geometrical figure which is large enough to contain the device (1);

(ii) a first position (10) outside the geometrical figure formed by guiding means (ABC), to which the device (1) can be affixed;

(iii) a second position (10) to which the device (1) can be affixed after being lifted over or under the closed loop(s) to form a relatively loose knot in the element (2), wherein said second position (10') is inside the geometrical figure formed by guiding means (ABC);

(iv) means for tightening the knot through a tensioning means (40); wherein means (i), (ii) and (iii) can be rotated with respect to means (iv).

In an embodiment, the invention relates to an apparatus (20) as described above, wherein the guiding means (ABC) comprises at least three separate guiding means parts, A, B and C, or comprises two separate guiding means A and BC, forming a geometrical figure which is large enough to contain the device (1).

In an embodiment, the invention relates to an apparatus (20) as described above, additionally comprising a translating means, capable of translating the device from position 10 to position 10', by lifting the device over or under and inside the one or more closed loops formed in the element (2) by the apparatus (20).

In an embodiment, the invention relates to an apparatus (20) as described above, wherein guiding means (ABC) can be retracted into or lifted away from the apparatus (20) in order to release element (2).

In an embodiment, the invention relates to an apparatus (20) as described above, wherein the diameter and/or location of part A of the guiding means with respect to position (10') defines the length of the element between knot and device.

In an embodiment, the invention relates to an apparatus (20) as described above, wherein one or more strands of the element are directed towards or away from the guiding means (ABC) by tensioning means (40).

In an embodiment, the invention relates to an apparatus (20) as described above, wherein part A of the guiding means is located closest to the end of the device (1) whereon the element (2) is fixed.

In an embodiment, the invention relates to an apparatus (20) as described above, wherein the element (2) is provided to the apparatus in the form of a spindle or bobbin or already cut, preferably capable of maintaining a certain tension on the element.

In an embodiment, the invention relates to an apparatus (20) as described above, wherein all movements or rotations of the apparatus are automated.

In an embodiment, the invention relates to an apparatus (20) as described above, wherein said translation means is a robotic arm.

In an embodiment, the invention relates to a method for making a knot in a flexible element connected to a device using the apparatus (20) according to any one of claims 1 to 10, comprising the steps of:

a) placing the device (1), to which the element (2) is attached, in the first position (10) on the apparatus (20), outside the area defined by guiding means (ABC);

b) rotating the guiding means (ABC) one or more times with respect to the tensioning means (40), thereby forming one or more closed loops in element (2);

c) translating the device (1) from its first position (10) to its second position (10') inside the area defined by guiding means (ABC), by lifting it over or under the closed loop(s) formed in step b);

d) releasing element (2) from guiding means (ABC), under constant tension by the tensioning means (40), thereby forming the final knot (3).

In an embodiment, the invention relates to a method as described above, wherein the number of rotations, translations and threading actions can be adjusted to tailor the thickness of the knot.

In an embodiment, the invention relates to a method as described above, which is automated.

In an embodiment, the invention relates to a method as described above, wherein the translation movement of device (1) is performed by a robotic arm.

In an embodiment, the invention relates to a method as described above, wherein the device is an intra uterine device (IUD), for contraceptive purposes or for intra uterine treatment, a tampon, a hearing aid, or the like.

The invention claimed is:

1. An apparatus (20) that receives a contraceptive intrauterine device (1) which apparatus (20) makes a knot in a flexible element (2) attached to the contraceptive intrauterine device (1, the apparatus (20) comprising: (i) a guiding means (ABC) that guides the flexible element (2), wherein the guiding means (ABC) comprises at least 3 separate guiding means parts and which guiding means (ABC) forms a geometrical volume which is dimensioned to contain the contraceptive intrauterine device (1) disposed in a flat horizontal orientation entirely; (ii) a first fixating means that fixes the contraceptive intrauterine device (1) at a first position (10) outside the geometrical volume formed by the guiding means (ABC); (iii) a second fixating means that fixes the contraceptive intrauterine device (1) at a second position (10') entirely within the geometrical volume formed by the guiding means (ABC), wherein the contraceptive intrauterine device (1) is disposed in the flat horizontal orientation; and (iv) a tensioning means (40) located outside the guiding means (ABC), wherein the tensioning means tightens the knot and comprises one or more of a coil, spring, weight or suction device; wherein the guiding means (ABC), first fixating means and second fixating means are disposed in a mutually fixed positional relation, and are configured to spin as a group constrained around a single axis of rotation positioned within the guiding means (ABC), relative to the tensioning means (40), and the tensioning means is disposed in fixed positional relation to the single axis of rotation, and wherein the contraceptive intrauterine device (1) has a flat form and is insertable into an external body orifice.

2. The apparatus (20) according to claim 1, wherein one of the at least three separate guiding means parts (A) is located closest to the second position (10') corresponding to an end of the contraceptive intrauterine device (1) onto which the flexible element (2) is fixed.

3. The apparatus (20) according to claim 2, wherein a diameter or a location of said one of the at least three separate guiding means parts (A) with respect to the second position (10') defines the length of the flexible element (2) between the knot and the contraceptive intrauterine device (1).

4. The apparatus (20) according to claim 1, additionally comprising a translational displacer that translates the contraceptive intrauterine device (1) from the first position (10) to the second position (10'), by lifting the contraceptive intrauterine device (1) over or under and inside one or more closed loops formed in the flexible element (2) by the apparatus (20).

5. The apparatus (20) according to claim 4, wherein said translational displacer is a robotic arm.

6. The apparatus (20) according to claim 1, wherein the guiding means (ABC) is configured for retraction into or lifting away from the apparatus (20) in order to release the flexible element (2).

7. The apparatus (20) according to claim 1, wherein the flexible element comprises strands, the strands being directed towards or away from the guiding means (ABC) by the tensioning means (40).

8. The apparatus (20) according to claim 1, wherein the flexible element (2) is provided to the apparatus (20) in the form of a spindle or bobbin or already cut.

9. The apparatus (20) according to claim 8, wherein the flexible element (2) is capable of maintaining tension.

10. The apparatus (20) according to claim 1, wherein all movements or rotations of the apparatus (20) are automated.

11. A combination comprising an apparatus (20) and a contraceptive intrauterine device (1), wherein the apparatus (20) receives the contraceptive intrauterine device (1) and makes a knot in a flexible element (2) attached to the contraceptive intrauterine device (1), the apparatus (20) comprising: (i) a guiding means (ABC) that guides the flexible element (2), wherein the guiding means (ABC) comprises at least 3 separate guiding means parts, which guiding means (ABC) forms a geometrical volume which is dimensioned to contain the contraceptive intrauterine device (I) disposed in a flat horizontal orientation entirely; (ii) a first fixating means at a first position (10) that fixes the contraceptive intrauterine device (1) outside the geometrical volume formed by the guiding means (ABC); (iii) a second fixating means at a second position (10') that fixes the contraceptive intrauterine device (1) disposed in the flat horizontal orientation entirely within the geometrical volume formed by the guiding means (ABC); and (iv) a tensioning means (40) located outside the guiding means (ABC), wherein the tensioning means (40) tightens the knot and comprises one or more of a coil, spring, weight or suction device; wherein the guiding means (ABC), first fixating means and second fixating means are disposed in a mutually fixed positional relation, and are configured to spin as a group constrained around a single axis of rotation positioned within the guiding means (ABC), relative to the tensioning means (40), and the tensioning means (40) is disposed in fixed positional relation to the single axis of rotation, and wherein the contraceptive intrauterine device (1) has a flat form and is insertable into an external body orifice.

12. The combination according to claim 11, wherein the contraceptive intrauterine device (1) contains a drug.

13. The combination according to claim 11, wherein one of the at least three separate guiding means parts (A) is located closest to the second position (10') corresponding to an end of the contraceptive intrauterine device (1) onto which the flexible element (2) is fixed.

14. The combination according to claim 13, wherein a diameter or a location of said one of the separate guiding means parts (A) with respect to the second position (10') defines the length of the flexible element (2) between the knot and the contraceptive intrauterine device (1).

15. The combination according to claim 11, additionally comprising a translational displacer that translates the contraceptive intrauterine device (1) from the first position (10) to the second position (10'), by lifting the contraceptive intrauterine device (1) over or under and inside one or more closed loops formed in the flexible element (2) by the apparatus (20).

16. The combination according to claim 15, wherein said translational displacer is a robotic arm.

17. The combination according to claim 11, wherein the guiding means (ABC) is configured for retraction into or lifting away from the apparatus (20) in order to release the flexible element (2).

18. The combination according to claim 11, wherein the flexible element comprises strands, the strands being directed towards or away from the guiding means (ABC) by the tensioning means (40).

19. The combination according to claim 11, wherein the flexible element (2) is provided to the apparatus (20) in the form of a spindle or bobbin.

20. The combination according to claim 11, wherein all movements or rotations of the apparatus (20) are automated.

21. The combination according to claim 11, wherein the flexible element (2) is capable of maintaining tension.

22. The combination according to claim 11, wherein the contraceptive intrauterine device (1) comprises a T-shape.

* * * * *